United States Patent
Dreisbach et al.

(10) Patent No.: US 7,193,102 B2
(45) Date of Patent: Mar. 20, 2007

(54) PROCESS FOR THE RACEMATE RESOLUTION OF 3-AMINOPENTANENITRILE

(75) Inventors: Claus Dreisbach, Leichlingen (DE); Björn Schlummer, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 255 days.

(21) Appl. No.: 10/690,260

(22) Filed: Oct. 21, 2003

(65) Prior Publication Data

US 2004/0087811 A1 May 6, 2004

(30) Foreign Application Priority Data

Oct. 22, 2002 (DE) ................................ 102 49 339

(51) Int. Cl.
*C07C 255/03* (2006.01)
(52) U.S. Cl. ...................... 558/451; 558/463
(58) Field of Classification Search ............... 558/451, 558/463
See application file for complete search history.

(56) References Cited

U.S. PATENT DOCUMENTS

| | | | |
|---|---|---|---|
| 3,808,254 A | 4/1974 | Matthews | 260/465 D |
| 4,072,698 A | 2/1978 | Hylton et al. | 260/465 E |
| 4,260,556 A | 4/1981 | Kluger et al. | 260/465.5 R |
| 4,496,474 A | 1/1985 | Reck | 252/311.5 |
| 5,070,202 A | 12/1991 | Herkes | 544/402 |
| 5,902,883 A | 5/1999 | Herkes | 544/402 |
| 2004/0002615 A1 | 1/2004 | Allen et al. | 558/452 |

OTHER PUBLICATIONS

Williams et al., Isolation and Structure Determination of Obyanamide, a Novel Cytotoxic Cyclic Depsipeptide from the Marine Cyanobacterium *Lyngbya confervoides*. J. Nat. Prod. 2002, 65, pp. 29-31.*

J. Nat. Prod., (month unavailable), 2002, 65, pp. 29-31, Philip G. Williams et al, "Isolation and Structure Determination of Obyanamide, a Novel Cytotoxic Cyclic Depsipeptide from the Marine Cyanobacterium *Lyngbya confervoides*".

Jacques, Jean et al.: "Enantiomers, Racemates, and Resolutions" 1981, Wiley-Interscience Publication, New York, XP002292433 *Seite 253-Seite 256* * Seite 259-Seite 261* * Seite 396-Seite 399*.

Williams, Philip G. et al.: J. Nat. Prod., Bd. 65, 2002, Seiten 29-31, XP002292432 *Seite 30-Seite 31*.

* cited by examiner

*Primary Examiner*—James O. Wilson
*Assistant Examiner*—Ebenezer Sackey
(74) *Attorney, Agent, or Firm*—Michael A. Miller

(57) ABSTRACT

By means of a new process for the resolution of racemic 3-aminopentanenitrile, enantiomerically enriched 3-aminopentanenitrile or its salts can be obtained. For this, racemic 3-aminopentanenitrile is reacted with an enantiomerically enriched organic acid and one of the two diastereomeric salts formed is separated off and then converted into the enantiomerically enriched 3-aminopentanenitrile or its salts.

15 Claims, No Drawings

PROCESS FOR THE RACEMATE RESOLUTION OF 3-AMINOPENTANENITRILE

BACKGROUND OF THE INVENTION

1. Field of the Invention

The present invention relates to a process for the resolution of racemic 3-amino-pentanenitrile with obtainment of enantiomerically enriched 3-aminopentanenitrile or its salts by reaction of racemic 3-aminopentanenitrile with enantiomerically enriched organic acids.

2. Brief Description of the Prior Art (R)-3-Aminopentanenitrile and its salts are important starting materials for the synthesis of pharmaceutical active compounds. Since the pharmaceutical action is often attributed to only one isomer, it is desirable to prepare or to make available this desired enantiomer in high optical purity. The aim is therefore to plan the synthesis such that racemic intermediate compounds are separated into their enantiomers, in order to obtain homochiral products.

In U.S. Pat. No. 4,260,556, the preparation of racemic 3-aminopentanenitrile by reaction of 2-pentenenitrile with ammonia in the presence of a metallic catalyst is described.

In U.S. Pat No. 4,496,474, the reaction of 2-pentenenitrile with alkylamines with the formation of the corresponding racemic cyano compounds is disclosed. In EP-A0 449 297, an improved variant of this basic reaction of 2-pentenenitrile with alkylamines in the presence of 15–60% by weight of water is described.

U.S. Pat. No. 5,902,883 describes a process for the cyanobutylation of ammonia, alkylamines or hydrazine with 3- and 4-pentenenitrile, or mixtures thereof, with formation of the racemic alkylaminonitriles.

In the aforementioned prior art, no indication at all of a separation of the racemic mixtures obtained in each case is given.

In J. Nat. Prod. 65 (2002), 29–31, the preparation of enantiomerically pure (R)- and (S)-3-aminopentanenitrile by constructive synthesis starting from (R)- or (S)-2-aminobutanol is described.

The preparation of enantiomerically pure or enantiomerically enriched (R)- or (S)-3-aminopentanenitrile by resolution of racemic 3-aminopentanenitrile has hitherto not been described anywhere in the prior art.

Since the only method for the synthesis of enantiomerically enriched 3-amino-pentanenitrile, known from J. Nat. Prod. 65 (2002), 29–31, is very laborious, the object of the present invention consisted in making available a suitable process for the resolution of racemic 3-aminopentanenitrile with enrichment of one of the two enantiomers.

SUMMARY OF THE INVENTION

The invention relates to a process for the obtainment of enantiomerically enriched 3-aminopentanenitrile or its salts from racemic 3-aminopentanenitrile by 1) reaction of racemic 3-aminopentanenitrile with an enantiomerically enriched organic acid with formation of two diastereomeric salts of 3-aminopentanenitrile and the organic acid,
2) separation of one diastereomeric salt from the reaction mixture and
3) conversion of this diastereomeric salt into the enantiomerically enriched 3-aminopentanenitrile or its salts.

DETAILED DESCRIPTION OF THE INVENTION

Enantiomerically enriched 3-aminopentanenitrile in the sense of the invention means the enantiomerically pure compounds (R)-3-aminopentanenitrile and (S)-3-aminopentanenitrile or mixtures of the two enantiomers (R)-3-aminopentanenitrile and (S)-3-aminopentanenitrile in which one enantiomer is present in an enantiomeric excess, below also called ee, in comparison with the other enantiomer. Preferably, this enantiomeric excess is 2 to 100% ee, particularly preferably 60% to 100% and very particularly preferably 85 to 100%. A definition of the ee value is indicated in the context of the examples of this application.

Enantiomerically enriched organic acids which can be employed in the sense of this invention are enantiomerically enriched carboxylic acids, enantiomerically enriched sulphonic acids or enantiomerically enriched phosphoric acids.

The use of enantiomerically enriched carboxylic acids is preferred. It is possible in the process according to the invention to employ here, for example:

hydroxycarboxylic acids such as, for example, (L)-(+)-lactic acid, (L)-(−)-malic acid and (L)-(−)-tartaric acid and their derivatives (S)-(−)-phenylcarbamoyllactic acid, (−)-O,O'-dibenzoyl-(L)-tartaric acid and (−)-di-O-p-toluyl-(L)-tartaric acid, (S)-(+)-mandelic acid and its derivative (S)-methoxyphenylacetic acid, and gulonic acids such as (−)-diacetone-2-keto-L-gulonic acid, substituted propionic acids such as, for example, (S)-(+)-6-methoxy- -methyl-2-naphthylacetic acid, (S)-(+)-2-(4-isobutylphenyl)-propionic acid and 2-(2-fluoro-4-biphenylyl)-propionic acid, N-protected amino acid derivatives such as, for example, (L)-N-Boc-alanine, (L)-N-Boc-aspartic acid, (L)-N-Boc-histidine, (L)-N-Boc-isoleucine, (L)-N-Boc-leucine, (L)-N-Boc-methionine, (L)-N-Boc-phenylalanine, (L)-N-Boc-proline, (L)-N-Boc-serine, (L)-N-Boc-threonine, (L)-N-Boc-tyrosine, (L)-N-Boc-valine and (L)-N-acetyl-leucine, menthol derivatives such as (−)-menthoxyacetic acid or (S)-(−)-2-pyrrolidinone-5-carboxylic acid.

Analogously, all enantiomers of the specific carboxylic acids mentioned beforehand can also be employed.

In order to obtain (S)-enantiomerically enriched 3-aminopentanenitrile or its salts, the following carboxylic acids are preferably employed in step 1) of the process according to the invention: (S)-methoxyphenylacetic acid, (−)-menthoxyacetic acid and (S)-(−)-2-pyrrolidinone-5-carboxylic acid. (−)-Diacetone-2-keto-L-gulonic acid is particularly preferred. The mother liquor formed in the separation of the diastereomeric salt in step 2) of the process according to the invention can be worked up further and then correspondingly yields the other (R)-enantiomerically enriched 3-aminopentanenitrile or its salts.

Preferred carboxylic acids for the obtainment of the (R)-enantiomerically enriched 3-aminopentanenitriles are substituted propionic acids and N-protected amino acid derivatives. (L)-N-Boc-isoleucine and (L)-N-Boc-serine are particularly preferred. The mother liquor formed in the separation of the diastereomeric salt in step 2) of the process according to the invention can be worked up further and then correspondingly yields the (S)-enantiomerically enriched 3-aminopentanenitrile or its salts.

Enantiomerically enriched organic acids of this type such as carboxylic acids, sulphonic acids or phosphoric acid, preferably carboxylic acids, are commercially obtainable. The term "enantiomerically enriched organic acid/carboxylic acid/sulphonic acid/phosphoric acid" in the sense of this invention means the respective enantiomerically pure organic acids/carboxylic acids/sulphonic acids/phosphoric acids or mixtures of the respective enantiomers in which one enantiomer is presence in an enantiomeric excess, below also called ee, in comparison with the other enantiomer. Preferably, this ee value is 10–100%, particularly preferably 60–100% and very particularly preferably 95–100%.

The reaction of the racemic 3-aminopentanenitrile with the enantiomerically enriched organic acid with formation of two diastereomeric salts in step 1) of the process according to the invention is expediently carried out in a temperature range from 0° C. up to the decomposition temperature of the reactants, preferably in a range from 20 to 120° C. The reaction is particularly preferably carried out in a range from 60 to 80° C.

The reaction in step 1) is customarily carried out in the presence of a solvent. The solvents used can be polar or non-polar organic solvents, for example ethers, preferably dialkyl ethers, in particular diethyl ether and tert-butyl methyl ether, or cyclic ethers, in particular tetrahydrofuran, straight-chain or branched $C_1$–$C_{10}$-alcohols, preferably methanol, ethanol, n-propanol or iso-propanol, straight-chain or branched $C_1$–$C_{10}$-alcohol derivatives, such as partly halogenated $C_1$–$C_{10}$-alcohols, mononuclear and polynuclear aromatic carbocyclic and heterocyclic hydrocarbons, preferably toluene, aliphatic $C_1$–$C_{10}$ hydrocarbons, and functionalized hydrocarbons such as nitriles, for example acetonitrile, carboxylic acid esters, preferably ethyl acetate, ketones and halogen compounds. The amount of the solvent employed is not critical.

The reactants, i.e. the enantiomerically enriched organic acid and the racemic 3-aminopentanenitrile, can be employed in any desired amounts. Preferably, 0.1–1 equivalent of the organic acid, particularly preferably approximately 0.5 equivalent of the organic acid, is employed.

By means of the reaction of the racemic 3-aminopentanenitrile with the enantiomerically enriched organic acid, two diastereomeric salts of 3-aminopentanenitrile and the organic acid are formed in the process according to the invention. These are, for example, the diastereomeric salts (S)-3-aminopentanenitrile L-(−)-diacetone-2-ketogulonate,
(S)-3-aminopentanenitrile (S)-1-methoxy-1-phenylacetate,
(R)-3-aminopentanenitrile N-Boc-L-isoleucinate,
(R)-3-aminopentanenitrile N-Boc-L-leucinate,
(R)-3-aminopentanenitrile N-Boc-L-serinate,
(S)-3-aminopentanenitrile (S)-(−)-2-pyrrolidinone-5-carboxylate,
(R)-3-aminopentanenitrile (S)-(+)-6-methoxy-α-methyl-2-naphthylacetate,
(R)-3-aminopentanenitrile (S)-(+)-2-(4-isobutylphenyl)-propioncarboxylate,
(R)-3-aminopentanenitrile (S)-(−)-O-(phenylcarbamoyl)-lactate,
(R)-3-aminopentanenitrile (−)-O,O'-dibenzoyl-L-tartrate,
(R)-3-aminopentanenitrile (−)-di-O-p-toluyl-L-tartrate,
(S)-3-aminopentanenitrile (−)-menthoxyacetate,
(R)-3-aminopentanenitrile N-acetyl-L-leucinate and their respective enantiomers.

During the reaction in step 1), one of the two diastereomeric salts customarily precipitates in the form of a solid. The separation of this diastereomeric salt from the reaction mixture is customarily carried out in step 2) by filtering off or centrifuging off.

The reaction mixture which remains after filtering off the diastereomeric salt can be worked up if desired to obtain the second diastereomeric salt.

In an alternative embodiment of the process according to the invention, it can be expedient to subject the diastereomeric salt separated off as a solid in step 2) to one or more recrystallizations before in step 3) of-the process before the enantiomerically enriched 3-aminopentanenitrile or its salts are obtained. For these recrystallizations, the use of the solvents already mentioned in step 1) has proved suitable.

In step 3), the desired enantiomerically enriched 3-aminopentanenitrile or its salts are then obtained from the separated-off diastereomeric salt of the desired enantiomerically enriched 3-aminopentanenitrile or its salts. This can take place by chemical means.

For this, the diastereomeric salt is reacted with a base which is stronger than the amine function in 3-aminopentanenitrile, e.g. with alkali metal hydroxides, alkaline earth metal hydroxides, preferably sodium hydroxide or potassium hydroxide, alkali metal carbonates or alkaline earth metal carbonates, preferably sodium carbonate or potassium carbonate, and subsequently extracted with an organic solvent. The solvents employed can be the organic solvents already mentioned previously. Expediently, 1–5 N solutions of the base at a temperature of 0 to 100° C. are employed. The use of 1N sodium hydroxide solution at a temperature of 15 to 40° C. with subsequent extraction by dichloromethane is particularly preferred. During this reaction of the diastereomeric salt with a base, the enantiomerically enriched 3-aminopentanenitrile is obtained as such, i.e. as the free base.

Alternatively to this, the diastereomeric salt can also be reacted in an organic solvent with a strong acid which is stronger than the enantiomerically enriched organic acid employed in step 1). In this connection, for example, hydrochloric acid, hydriodic acid, hydrobromic acid, hydrofluoric acid, sulphuric acid, nitric acid, perchloric acid, phosphoric acid or methanesulphonic acid is employed. Hydrochloric acid, hydrobromic acid, sulphuric acid and methanesulphonic acid are preferred. This reaction in step 3) is carried out at a temperature in the range from 0° C. up to approximately the decomposition temperature of the reactants, preferably in a range from 20 to 150° C. and particularly preferably in a range from 40 to 90° C. The solvents employed can be the organic solvents already mentioned previously. Preferably, ethers, particularly preferably tert-butyl methyl ether, are employed as solvents. In this variant, the desired enantiomerically enriched 3-aminopentanenitrile is obtained directly as the salt of the strong acid. The following salts of 3-aminopentanenitrile are obtained, for example:

enantiomerically enriched 3-aminopentanenitrile fluoride
enantiomerically enriched 3-aminopentanenitrile chloride
enantiomerically enriched 3-aminopentanenitrile bromide
enantiomerically enriched 3-aminopentanenitrile iodide
enantiomerically enriched 3-aminopentanenitrile sulphate
enantiomerically enriched 3-aminopentanenitrile hydrogensulphate
enantiomerically enriched 3-aminopentanenitrile phosphate
enantiomerically enriched 3-aminopentanenitrile hydrogenphosphate
enantiomerically enriched 3-aminopentanenitrile dihydrogenphosphate
enantiomerically enriched 3-aminopentanenitrile nitrate
enantiomerically enriched 3-aminopentanenitrile perchlorate.

The salts can be used for the preparation of pharmaceutical active compounds.

EXAMPLES

In all examples below, the optical purity of the (R)-or (S)-3-aminopentanenitrile is determined by gas chromatography on a chiral column material (gamma-Dex 225) and indicated by means of the ee ("enantiomeric excess") (S) or (R) value defined below.

The ee value is given here by means of the following formulae:

$$ee(S) = \frac{m(S) - m(R)}{m(S+R)} \times 100\%$$

$$ee(R) = \frac{m(R) - m(S)}{m(S+R)} \times 100\%$$

where ee (S) or ee (R) is the optical purity of the enantiomer S or R, m(S) is the amount of substance of the enantiomer S and m(R) is the amount of substance of the enantiomer R. (Examples: for a racemate: R=S=>ee=0; for the pure (S) form: ee (S)=100%; for a ratio of S:R=9:1, ee (S)=80%)

Example 1

Racemate resolution using (−)-diacetone-2-keto-L-gulonic acid 1.50 g (15.3 mmol) of 3-aminopentanenitrile are dissolved in the amount of the respective solvent indicated in Table 1a. 1.77 g (7.65 mmol) of (−)-diacetone-2-keto-L-gulonic acid are added to this solution in one portion. The suspension is heated to boiling for 5 minutes. After cooling to 20° C., the product formed as a solid is filtered off and dried at 40° C. under reduced pressure for 10 hours. The product is then dissolved in 20 ml of 1N sodium hydroxide solution. The aqueous phase is extracted twice with 10 ml each time of dichloromethane. The solvent of the combined organic phases is distilled off under reduced pressure. The yields and ee values achieved are indicated in Table 1a.

TABLE 1a

| Solvent | EtOH | Toluene | MTBE | EtOAc | CH₃CN | MeOH |
|---|---|---|---|---|---|---|
| Amount (ml) | 60 | 75 | 90 | 40 | 75 | 45 |
| ee (S) (%) | 69.5 | 35.2 | 17.6 | 38.6 | 42.8 | 57.3 |
| Yield (%) | 33.4 | 40.0 | 56.0 | 37.0 | 37.0 | 31.0 |

EtOH = ethanol, MTBE = methyl tert-butyl ether, EtOAc = ethyl acetate, MeOH = methanol

Example 1b

By reaction of racemic 3-aminopentanenitrile with (−)-diacetone-2-keto-L-gulonic acid in analogy to Example 1 in ethanol as a solvent, a precipitate of the diastereomeric salt is obtained. This is subjected to a further recrystallization, whereby the optical purity and thus the ee value of the (S)-enantiomerically enriched 3-aminopentanenitrile can be further increased. The ee(S) value of the diastereomeric salt employed for the recrystallization is, after an extraction carried out in analogy to Example 1, 59.6.

For the recrystallization, 1.5 g of the diastereomeric salt are dissolved at boiling temperature in the amount of the respective solvent in each case indicated in Table 1b. The further work-up of the salt precipitating on cooling is carried out as described for Example 1.

TABLE 1b

| Solvent | EtOH | CH₃CN | Toluene | MTBE | EtOAc | MeOH |
|---|---|---|---|---|---|---|
| Amount (ml) | 40 | 40 | 50 | 40 | 50 | 35 |
| ee (S) (%) | 67.8 | 65.6 | 61.5 | 61.3 | 64.2 | 82.4 |
| Yield (%) | 93.3 | 94.7 | 98.0 | 98.7 | 94.4 | 68.0 |

Example 2

Racemate resolution using (S)-methoxyphenylacetic acid 1.50 g (15.3 mmol) of 3-aminopentanenitrile are dissolved in the amount of the respective solvent indicated in Table 2. 1.27 g (7.64 mmol) of (S)-methoxyphenylacetic acid are added to this solution in one portion. The suspension is heated to boiling for 5 minutes. After cooling to 20° C., the product forming as a solid is filtered off and dried at 40° C. under reduced pressure for 10 hours. The product is then dissolved in 20 ml of 1N sodium hydroxide solution. The aqueous phase is extracted twice with 10 ml each time of dichloromethane. The solvent of the combined organic phases is distilled off under reduced pressure.

The yields and ee values achieved are indicated in Table 2.

TABLE 2

| Solvent | EtOH | Toluene | MTBE | EtOAc | CH₃CN | MeOH |
|---|---|---|---|---|---|---|
| Amount (ml) | 60 | 40 | 45 | 30 | 15 | 15 |
| ee (S) (%) | 50.7 | 54.7 | 55.8 | 49.7 | 71.6 | 81.6 |
| Yield (%) | 40.0 | 28.0 | 3.0 | 31.0 | 53.0 | 15.0 |

Example 3

Racemate resolution using (S)-(+)-6-methoxy-α-methyl-2-naphthylacetic acid 1.50 g (15.3 mmol) of 3-aminopentanenitrile are dissolved in 10 ml of ethanol. 1.76 g (7.64 mmol) of (S)-(+)-6-methoxy-α-methyl-2-naphthylacetic acid are added to this solution in one portion. The suspension is heated to boiling for 5 minutes. After cooling to 20° C., the product forming as a solid is filtered off and dried at 40° C. under reduced pressure for 10 hours. The product is then dissolved in 20 ml of 1N sodium hydroxide solution. The aqueous phase is extracted twice with 10 ml each time of dichloromethane. The solvent of the combined organic phases is distilled off under reduced pressure.

0.60 g (40.0%) of (R)-3-aminopentanenitrile is obtained as a colourless liquid. The ee (R) value is 27.4%.

Example 4

Racemate resolution using (S)-(+)-2-(4-isobutylphenyl)propionic acid 1.50 g (15.3 mmol) of 3-aminopentanenitrile are dissolved in 10 ml of ethanol. 1.58 g (7.64 mmol) of (S)-(+)-2-(4-isobutylphenyl)-propionic acid are added to this solution in one portion. The suspension is heated to boiling for 5 minutes. After cooling to 20° C., the product forming as a solid is filtered off and dried at 40° C. under reduced pressure for 10 hours. The product is then dissolved in 20 ml of 1N sodium hydroxide solution. The aqueous phase is extracted twice with 10 ml each time of dichloromethane. The solvent of the combined organic phases is distilled off under reduced pressure.

0.78 g (52.0%) of (R)-3-aminopentanenitrile is obtained as a colourless liquid. The ee(R) value is 2.4%.

Example 5

Racemate resolution using (L)-N-Boc-isoleucine 1.50 g (15.3 mmol) of 3-aminopentanenitrile are dissolved in the amount of solvent used indicated in Table 3a. 1.77 g (7.64 mmol) of (L)-N-Boc-isoleucine are added to this solution in one portion. The suspension is heated to boiling for 5 minutes. After cooling to 20° C., the product forming as a solid is filtered off and dried at 40° C. under reduced pressure for 10 hours. The product is then dissolved in 20 ml of 1N sodium hydroxide solution. The aqueous phase is extracted twice with 10 ml each time of dichloromethane. The solvent of the combined organic phases is distilled off under reduced pressure.

The yields and ee values achieved are indicated in Table 3a.

TABLE 3a

| Solvent | EtOH | Toluene | MTBE | EtOAc | CH$_3$CN |
|---|---|---|---|---|---|
| Amount (ml) | 10 | 15 | 15 | 15 | 15 |
| ee (R) (%) | 92.2 | 68.7 | 85.7 | 81.4 | 82.5 |
| Yield (%) | 6.7 | 42.0 | 35.0 | 36.0 | 29.0 |

Example 5b

By reaction of racemic 3-aminopentanenitrile with (L)-N-Boc-isoleucine in analogy to Example 5 in ethanol as a solvent, a precipitate of the diastereomeric salt is obtained. This is subjected to a further recrystallization, whereby the optical purity and thus the ee value of the (R)-enantiomerically enriched 3-aminopentanenitrile can be further increased. The ee(R) value of the diastereomeric salt employed for the recrystallization is, after an extraction carried out in analogy to Example 5, 90.4.

For the recrystallization, 1.25 g of the diastereomeric salt are dissolved at boiling temperature in the amount of the respective solvent indicated in Table 3b. The further work-up of the salt precipitating on cooling is carried out as described for Example 5.

TABLE 3b

| Solvent | EtOH | CH$_3$CN | Toluene | MTBE | EtOAc | MeOH |
|---|---|---|---|---|---|---|
| Amount (ml) | 4 | 10 | 5 | 45 | 5 | 2 |
| ee (R) (%) | 98.5 | 98.3 | 95.3 | 98.7 | 96.8 | 98.0 |
| Yield (%) | 34.9 | 32.2 | 80.6 | 69.8 | 56.4 | 29.5 |

Example 6

Racemate resolution using (L)-N-Boc-isoleucine with subsequent precipitation of the enantiomerically enriched 3-aminopentanenitrile methanesulphonate 33.05 g (336.7 mmol) of 3-aminopentanenitrile are dissolved in 830 ml of tert-butyl methyl ether. 39.0 g (168.6 mmol) of (L)-N-Boc-isoleucine are added to this solution in one portion. The suspension is heated to boiling for 5 minutes. After cooling to 20° C., the product forming as a solid is filtered off and washed twice with 50 ml each time of tert-butyl methyl ether. The product is recrystallized once from 1650 ml of tert-butyl methyl ether. After cooling to 20° C., the solid is filtered off with suction and washed twice with 50 ml of tert-butyl methyl ether.

35.0 g of a colourless solid are obtained.

This is suspended in 700 ml of tert-butyl methyl ether. 10.22 g (106.3 mmol) of methanesulphonic acid are then added dropwise to this suspension. The suspension is heated to boiling for 5 minutes. After cooling to 20° C., the solid is filtered off with suction, washed twice with 25 ml each time of tert-butyl methyl ether and dried under reduced pressure at 50° C. for 10 hours.

19.8 g (30.3%) of (R)-3-aminopentanenitrile methanesulphonate are obtained as a colourless solid.

For the determination of the optical purity, 1 g of the product obtained is dissolved in 20 ml of 1N sodium hydroxide solution and the solution is extracted twice with 10 ml each of dichloromethane. After removing the solvent under reduced pressure, the ee value is determined from the residue by gas chromatography. The ee (R) value is 99.0%.

NMR (400 MHz, D$_2$O): (ppm)=1.00 (t, J=7.5 Hz, 3H), 1.83 (dt, J=7.3/7.3 Hz, 2H), 2.80 (s, 3H), 3.02 (d, J=5.3 Hz, 2H), 3.63 (tt, J=6.3/6.3 Hz, 1H), 4.75 (s, 3H).

Melting range: 109–111° C.

| Elemental analysis: | |
|---|---|
| calc.: C = 37.11 | fnd.: C = 37.3 |
| calc.: H = 7.27 | fnd.: H = 7.4 |
| calc.: N = 14.42 | fnd.: N = 14.1 |
| calc.: S = 16.48 | fnd.: S = 16.4 |

Example 7

Racemate resolution using (L)-N-Boc-serine 1.50 g (15.3 mmol) of 3-aminopentanenitrile are dissolved in the amount of solvent used indicated in Table 4. 1.57 g (7.64 mmol) of (L)-N-Boc-serine are added to this solution in one portion. The suspension is heated to boiling for 5 minutes. After cooling to 20° C., the product forming as a solid is filtered off and dried at 40° C. under reduced pressure for 10 hours. The product is then dissolved in 20 ml of 1N sodium hydroxide solution. The aqueous phase is extracted twice with 10 ml each time of dichloromethane. The solvent of the combined organic phases is distilled off under reduced pressure.

The yields and ee values achieved are indicated in Table 4.

TABLE 4

| Solvent | EtOH | Toluene | MTBE | EtOAc | CH$_3$CN | MeOH |
|---|---|---|---|---|---|---|
| Amount (ml) | 10 | 60 | 30 | 60 | 60 | 8 |
| ee (R) (%) | 70.0 | 70.7 | 76.0 | 80.4 | 63.3 | 86.8 |
| Yield (%) | 29.3 | 26.0 | 43.0 | 30.0 | 32.0 | 55.0 |

Example 8

Racemate resolution using (S)-(–)-phenylcarbamoyllactic acid 1.50 g (15.3 mmol) of 3-aminopentanenitrile are dissolved in 10 ml of ethanol. 1.60 g (7.64 mmol) of (S)-(–)-phenylcarbamoyllactic acid are added to this solution in one portion. The suspension is heated to boiling for 5 minutes. After cooling to 20° C., the product forming as a solid is filtered off and dried at 40° C. under reduced pressure for 10 hours. The product is then dissolved in 20 ml of 1N sodium hydroxide solution. The aqueous phase is extracted twice with 10 ml each time of dichloromethane. The solvent of the combined organic phases is distilled off under reduced pressure.

0.16 g (10.6%) of (R)-3-aminopentanenitrile is obtained as a colourless liquid. The ee (R) value is 23.1%.

Example 9

Racemate resolution using (–)-O,O'-dibenzoyl-(L)-tartaric acid 1.50 g (15.3 mmol) of 3-aminopentanenitrile are dissolved in 20 ml of ethanol. 2.74 g (7.64 mmol) of (–)-O,O'-dibenzoyl-(L)-tartaric acid are added to this solution in one portion. The suspension is heated to boiling for 5 minutes. After cooling to 20° C., the product forming as a solid is filtered off and dried at 40° C. under reduced pressure for 10 hours. The product is then dissolved in 20 ml of 1N sodium hydroxide solution. The aqueous phase is extracted twice with 10 ml each of dichloromethane. The solvent of the combined organic phases is distilled off under reduced pressure.

0.84 g (56.0%) of (R)-3-aminopentanenitrile is obtained as a colourless liquid. The ee (R) value is 4.4%.

Example 10

Racemate resolution using (–)-di-O-p-toluyl-(L)-tartaric acid 1.50 g (15.3 mmol) of 3-aminopentanenitrile are dissolved in 15 ml of ethanol. 2.95 g (7.64 mmol) of (–)-di-O-p-toluyl-(L)-tartaric acid are added to this solution in one portion. The suspension is heated to boiling for 5 minutes. After cooling to 20° C., the product forming as a solid is filtered off and dried at 40° C. under reduced pressure for 10 hours. The product is then dissolved in 20 ml of 1N sodium hydroxide solution. The aqueous phase is extracted twice with 10 ml each time of dichloromethane. The solvent of the combined organic phases is distilled off under reduced pressure.

1.04 g (69.3%) of (R)-3-aminopentanenitrile are obtained as a colourless liquid. The ee (R) value is 17.4%.

Example 11

Racemate resolution using (–)-menthoxyacetic acid 1.50 g (15.3 mmol) of 3-aminopentanenitrile are dissolved in 10 ml of ethanol. 1.64 g (7.64 mmol) of (–)-menthoxyacetic acid are added to this solution in one portion. The suspension is heated to boiling for 5 minutes. After cooling to 20° C., the product forming as a solid is filtered off and dried at 40° C. under reduced pressure for 10 hours. The product is then dissolved in 20 ml of 1N sodium hydroxide solution. The aqueous phase is extracted twice with 10 ml each time of dichloromethane. The solvent of the combined organic phases is distilled off under reduced pressure.

0.30 g (20.0%) of (S)-3-aminopentanenitrile is obtained as a colourless liquid. The ee (S) value is 55.2%.

Example 12

Racemate resolution using (S)-(–)-2-pyrrolidinone-5-carboxylic acid 1.50 g (15.3 mmol) of 3-aminopentanenitrile are dissolved in the amount of solvent used indicated in Table 5. 0.99 g (7.6 mmol) of (S)-(–)-2-pyrrolidinone-5-carboxylic acid is added to this solution in one portion. The suspension is heated to boiling for 5 minutes. After cooling to 20° C., the product forming as a solid is filtered off and dried at 40° C. under reduced pressure for 10 hours. The product is then dissolved in 20 ml of 1N sodium hydroxide solution. The aqueous phase is extracted twice with 10 ml each time of dichloromethane. The solvent of the combined organic phases is distilled off under reduced pressure.

The yields and ee values achieved are indicated in Table 5.

TABLE 5

| Solvent | EtOH | MTBE | EtOAc | CH$_3$CN |
|---|---|---|---|---|
| Amount (ml) | 15 | 15 | 15 | 15 |
| ee (S) (%) | 55.2 | 39.0 | 35.9 | 26.3 |
| Yield (%) | 29.3 | 43.0 | 30.0 | 32.0 |

Example 13

Racemate resolution using N-acetyl-(L)-leucine 1.50 g (15.3 mmol) of 3-aminopentanenitrile are dissolved in the amount of solvent used indicated in Table 6a. 1.32 g (7.64 mmol) of N-Acetyl-(L)-leucine are added to this solution in one portion. The suspension is heated to boiling for 5 minutes. After cooling to 20° C., the product forming as a solid is filtered off and dried at 40° C. under reduced pressure for 10 hours. The product is then dissolved in 20 ml of 1N sodium hydroxide solution. The aqueous phase is extracted twice with 10 ml each time of dichloromethane. The solvent of the combined organic phases is distilled off under reduced pressure.

The yields and ee values achieved are indicated in Table 6a.

TABLE 6a

| Solvent | EtOH | Toluene | MTBE | EtOAc | CH$_3$CN | MeOH |
|---|---|---|---|---|---|---|
| Amount (ml) | 15 | 25 | 25 | 25 | 25 | 15 |
| ee (R) (%) | 66.4 | 46.7 | 50.7 | 42.4 | 41.2 | 71.1 |
| Yield (%) | 46.0 | 47.0 | 50.0 | 48.0 | 45.0 | 25.0 |

Example 13b

By reaction of racemic 3-aminopentanenitrile with N-acetyl-(L)-leucine in analogy to Example 13 in ethanol as a solvent, a precipitate of the diastereomeric salt is obtained.

This is subjected to a further recrystallization, whereby the optical purity and thus the ee value of the (R)-enantiomerically enriched 3-aminopentanenitrile can be further increased. The ee(R) value of the diastereomeric salt employed for the recrystallization, after an extraction carried out in analogy to Example 13, is 56.0.

For the recrystallization, 1.2 g of diastereomeric salt are dissolved at boiling temperature in the respective amount of solvent in each case indicated in Table 6b. The further work-up of the salt precipitating on cooling is carried out as described for Example 13.

TABLE 6b

| Solvent | EtOH | CH$_3$CN | MeOH |
| --- | --- | --- | --- |
| Amount (ml) | 20 | 60 | 8 |
| ee (R) (%) | 78.8 | 65.3 | 87.4 |
| Yield (%) | 50.7 | 62.2 | 36.9 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for obtaining enantiomerically enriched 3-aminopentanenitrile or its salts from racemic 3-aminopentanenitrile comprising:
    1) reacting racemic 3-aminopentanenitrile with an enantiomerically enriched organic acid with the formation of two diastereomeric salts of 3-aminopentanenitrile and the organic acid;
    2) separating one diastereomeric salt from the reaction mixture; and
    3) converting the separated diastereomeric salt into the enantiomerically enriched 3-aminopentanenitrile or its salts.

2. The process according to claim 1 wherein the enantiomerically enriched organic acid is selected from enantiomerically enriched carboxylic acid, 1 enriched sulphonic acid, and enantiomerically enriched phosphoric acid.

3. The process according to claim 2 wherein the enantiomerically enriched carboxylic acid is selected from enantiomerically enriched hydroxy-carboxylic acid or its derivatives, enantiomerically enriched substituted propionic acid, enantiomerically enriched N-protected amino acid and enantiomerically enriched menthol derivative.

4. The process according to claim 1 wherein the enantiomerically enriched organic acid is selected from (L)-(+)-lactic acid, (L)-(−)-malic acid, (L)-(−)-tartaric acid or their derivatives, (S)-(−)-phenylcarbamoyllactic acid, (−)-O,O"-dibenzoyl-(L)-tartaric acid, (−)-di-O-p-toluyl-(L)-tartaric acid, (S)-(+)-6-methoxy-phenylacetic acid, gulonic acids, (S)-(+)-6-methoxy-methyl-2-naphthylacetic acid, (S)-(+)-2-(4-isobutylphenyl)-propionic acid, 2-(2-fluoro-4-biphenylyl)-propionic acid, (L)-N-Boc-alanine, (L)-N-Boc-aspartic acid, (L)-N-Boc-histidine, (L)-N-Boc-isoleucine, (L)-N-Boc-Leucine, (L)-N-Boc-methionine, (L)-N-Boc-phenylalanine, (L)-N-Boc-proline, (L)-N-Boc-serine, (L)-N-Boc-serine, (L)-N-Boc-threonine, (L)-N-Boc-tyrosine, (L)-N-Boc-valine, (L)-N-acetyl-leucine, (−)-methoxyacetic acid, or (S)-(−)-2-pyrrolidinone-5-carboxylic acid or their respective enantiomers.

5. The process according to claim 2 for the obtainment of (S)-enantiomerically enriched 3-aminopentanenitrile or its salts, wherein the enantiomerically enriched carboxylic acid is selected from (S)-methoxyphenyl-acetic acid, (−)-methoxyacetic acid and (S)-(−)-2-pyrrolidinone-5-carboxylic acid.

6. The process according to claim 2 for the obtainment of (R)-enantiomerically enriched 3-aminopentanenitrile or its salts, wherein the 1 enriched carboxylic acids is selected from substituted propionic acids and N-protected amino acids and their derivatives.

7. The process according to claim 1 wherein the reaction in step 1) is carried out at a temperature in a range from 0° C. up to the decomposition temperature of the reactants.

8. The process according to claim 1 wherein the reaction in step 1) is carried out in the presence of polar or non-polar organic solvents.

9. The according to claim 1 wherein the racemic 3-aminopentanenitrile is 0.1–1 equivalent of the 1 enriched organic acid is employed.

10. The process according to claim 1 wherein the conversion of the diastereomeric salt into the enantiomerically enriched 3-aminopentanenitrile in Step 3) is carried out by the reaction of the diastereomeric salt with a base which is stronger than the amine function in 3-amino-pentanenitrile.

11. The process according to claim 1 for the obtainment of a salt of the enantiomerically enriched 3-aminopentanenitrile, wherein the obtainment of the salt of the enantiomerically enriched 3-aminopentanenitrile in step 3) is carried out by reaction of the diastereomeric salt with an acid which is stronger than the enantiomerically enriched organic acid employed in step 1), with the formation of the enantiomerically enriched 3-aminopentanenitrile salt of this acid.

12. The process according to claim 11 for the obtainment of the chloride, bromide, sulphate, or methanesulphoneate salt of the enantiomerically enriched 3-aminopentanenitrile wherein the acid of step 3) is selected from hydrochloric acid, hydrobromic acid, hydrofluoric acid, sulphuric acid, nitric acid, perchloric acid, phosphoric acid, or and methanesulphonic acid.

13. The process according to claim 1 wherein the separation of the diastereomeric salt from the reaction mixture in step 2) is carried out by filtering off.

14. The process according to claim 13 wherein the reaction mixture which remains after filtering the diastereomeric salt in step 2) is worked up for the purpose of obtaining a second diastereomeric salt.

15. The process according to claim 1 wherein the diastereomeric salt separated from the reaction mixture in step 2) is additionally subjected to one or more recrystallizations before carrying out step 3).

* * * * *